(12) United States Patent
Stockel

(10) Patent No.: US 6,585,961 B1
(45) Date of Patent: Jul. 1, 2003

(54) ANTIMICROBIAL COMPOSITIONS

(76) Inventor: Richard F. Stockel, 475 Rolling Hills Rd., Bridgewater, NJ (US) 08807

( * ) Notice: Subject to any disclaimer, the term of this patent is extended or adjusted under 35 U.S.C. 154(b) by 0 days.

(21) Appl. No.: 10/016,611

(22) Filed: Nov. 30, 2001

(51) Int. Cl.[7] .............................. A61K 7/16; A61K 7/26; A61K 7/24; A61K 35/78
(52) U.S. Cl. ......................... 424/49; 424/58; 424/725; 424/55; 424/742
(58) Field of Search ........................... 424/725, 49, 58, 424/55, 742

(56) References Cited

U.S. PATENT DOCUMENTS

| | | |
|---|---|---|
| 4,657,758 A | 4/1987 | Goldemberg |
| 5,174,990 A | 12/1992 | Douglas |
| 5,298,238 A | 3/1994 | Hussein |
| 6,077,501 A * | 6/2000 | Sickora et al. |
| 6,245,321 B1 * | 6/2001 | Nelson et al. |

* cited by examiner

*Primary Examiner*—Christopher R. Tate
*Assistant Examiner*—Randall Winston

(57) ABSTRACT

Aqueous antimicrobial and biofilm removal compositions, comprising essential oils and certain cationic, anionic, amphoteric or non-ionic surfactants individually or in combination having an hydrophile-lipophile balance (HLB) of about 16 or above are effective oral mouthwashes and topical antimicrobial solutions. Optionally $C_2$, $C_3$, benzyl, 3-phenylpropanol or 2-phenylethanol alcohols can be added singularly or in combination from about 2 to about 20v/w %.

Other optically ingredients include antimicrobial enhances and biofilm removal agents e.g., chelating compounds and certain organic acids.

21 Claims, No Drawings

ANTIMICROBIAL COMPOSITIONS

BACKGROUND OF THE INVENTION

This invention relates to compositions comprising essential oils having antimicrobial activity with one or more cationic, anionic, or amphoteric surfactants having a hydrophilic-lipophilic balance (HLB) or about 16 or greater. In particular, this invention relates to the employment of the combined essential oils and surfactants as an effective antimicrobial and plaque removal oral rinse. Other uses are also contemplated such as a topical solution to kill microbes and remove biofilm from medical and dental equipment and tubing.

Essential oils have long been known to have some degree of antimicrobial properties and some degree of antiplaque activity. However, sufficient activity is lacking, until the present invention.

A wide variety of microorganisms are found in the oral cavity, and among these are gram-positive anaerobic rods associated with the development of plaque such as Corynebacterium, Nocardia, Neisseria, and Streptococci, such as S. mutens, S. bovis, S. salivarius, and gram-positive streptococci of the genus Peptostreptooccus.

In addition, there is also present in plaque relatively small amounts of other substances such as salivary proteins, carbohydrates, epithelial cells and leukocytes. These organisms play a key role in the etiology of plaque. The bacterial organisms associated with plaque formation produce a capsular material, which apparently causes the cells of the organism to adhere to each other, holding the plaque together and allowing for further growth. For example, one of the capsule forming bacteria, which occurs in large numbers in early plaque is Neisseria sicca.

Removal of plaque and/or calculus by a dentist is currently the only safeguard against serious gingival inflammation caused by the accumulation of significant amounts of plaque.

Conventional mouthwashes serve primarily to sweeten the breath, are formulated for that purpose, and are believed not to function in any in any significant way to loosen or remove plaque from the dental surfaces.

There is a definite need in the art for an oral hygiene composition which, when used alone, or in conjunction with a regular tooth brushing regime, renders the plaque present on the dental surface more susceptible to removal.

ESSENTIAL OILS

Essential oils which have the characteristic or flavor of the plant (or synthetically derived) from which they are obtained having long been used as antimicrobial agents. Most essential oils are composed of terpenes, oxygenated constituents, sesquiterpenes, and a small amount of a nonvolatile residue. The principal essential oil constituents can therefore be divided into two broad classes of organic compounds: those, which contain only carbon and hydrogen, and those, which contain carbon, hydrogen and oxygen.

The carbon-hydrogen essential oils include paraffins, olefins, aromatic hydrocarbons, terpenes (olefinic as well as mono and tricyclic) a few lower terpene homologs, sesquiterpenes (aliphatic as well as mono, bi, and tricyclic), diterpones, and azulenes. Of these the terpenes and sesquiterpenes are most characteristic of essential oils. The fundamental building block of the terpene series is the isoprene unit, sometimes called a hemiterpene. Two such units give rise to the terpenes; three to the sesquiterpenes, four, to the diterpenes.

The carbon hydrogen - oxygen essential oils usually represent the more soluble portion of the oil. In this very broad class are included alcohols, aldehydes, ketones, and esters. As in the case of the carbon-hydrogen essential oils, many types are to be found saturated and unsaturated aliphatic as well as aromatic compounds, and also terpenic and sesquiterpenic compounds (aliphatic, monocyclic, bicyclic, and in the case of the sesquiterpene compounds, even tricyclic). Other important constituents are phenols and phenolic ethers, acids (usually esterified), lactones, oxides, and coumarins. Of lesser importance are the furan derivatives, the coumarones, and the quinones.

As in the pharmaceutical industry where the chirality of the bioactivity drug can play an important part in the enhance activity, the same can be true with essential oils and their antimicrobial efficacy. When stereoisomerism occurs, the molecule can have enantiomers, which differ in structure only in the left - and right handedness of their orientations. Optical activity in essential oils exists primarily by having one or more chiral carbon atoms. Thus it is theoretically possible that one of the enantiomers has greater antimicrobial activity, then the racemic mixture. Of course, the separation of an optically active substance would require additional expense, and unless there was a dramatic improvement at relative low costs, this methodology would not be cost-effective. Nevertheless, the preparation or optically active separation resulting in a significant enhancement of antimicrobial and/or biofilm removal capability is incorporated into the body of this invention.

The following list illustrates the voluminous numbers of essential oils having varying degrees of antimicrobial activity (not all inclusive): anethol, anise oil, anol, bay oil, bergamot oil, camphor, carvacrol, carvone, cedar leaf oil, citronel, eucalyptol, eugenol, guaiacol, hinokitiol, Isoeugenol, lavender oil, lemon oil, d-limonene, linalool, menthol, methyl salicylate, mustard oil, oil of cajeput, oil of cubeb, oil of santal, osimen, peppermint oil, phenolics, phenyl salicylate, pimento, pine oil, rosemary oil, safrale sage oil, saligenin, sassafras oil, spearmint oil, storax, vanillin, wintergreen oil, and other similar constituents.

This invention is not limited by the above specific essential oils. Many of the above components can be further chemically modified to enhance antimicrobial activity and are therefore part of the specifications of this invention concerning essential oils.

Furthermore, the specification includes stereoisomers and/or geometrical isomers of essential oils having chirality, because it is known that there can be significant difference in antimicrobial activity between the isomers.

For the purpose of carrying out the experimental portion of this invention, the following well-known essential oils were utilized; thymol, menthol, eucalyptol, and methyl salicylate were used.

SURFACTANTS

Surfactants are often an important constituent of disinfectants. They are employed to achieve both uniform wetting of the surface to be treated and frequently an additional cleaning effect. This is why particular attention should be given to this group of substances when formulating a disinfectant, as there are many ways in which the two groups of compounds can interact. It is generally known that, for instance, anionic surfactants promote the inactivation of quaternary ammonium compounds. The same most likely applies to other positively charged biocides, e.g., betaines, guanidines, biguanides, etc. The inactivating effects are generally obtained with surfactant concentrations well above critical micelle concentration of about 0.75 to about 2.5 weight %.

In contrast at lower concentrations improvements of the biocide often occur. The cause of the improved action by additional of low quantities of surfactants is considered to be an accumulation of the agent within micelles of the surfactant which adsorb at the microorganism cell wall. The active substance thus becomes enriched at the cell wall which means that a lower does is required for the desired effect. The property of surfactant at a higher concentration to inhibit the action of antimicrobial agents is attributed both to complexing and solubilizing in surfactant micelles. In both cases, the availability of full antimicrobial active substance is reduced.

ALCOHOL

Several mouthwashes that have been marketed for the reduction of bacteria and the prevention of plaque build-up generally rely on a combination of biocides and ethanol.

Commercial products contain up to 26.9% ethanol. However, the use of alcohol containing formulations tends to produce unpleasant side effects including pain and stinging of the oral mucous, foul aftertaste and discoloration of teeth. The use of alcohol in mouthwashes is being scrutinized by various government agencies due to some adverse physiological reactions, which are delineated in the literature including an increase in oral cancer. There are also societal advantages to a non-alcohol mouthwash, since it would discourage alcoholics from imbibing with the product. Hospitals would be more predisposed to purchase these non-alcohol formulations.

Therefore, where required or desired it is possible to have a no alcohol product, a low alcohol product (~5 to~15%) or a high alcohol product (up to 26.9%) by using the teachings of this invention.

DESCRIPTION OF THE INVENTION

The term surfactant is a contraction of surface-active agent. Surfactants are characterized by the following features. These amphipathic molecules are composed of groups of opposing solubility tendencies, typically an oil-soluble hydrocarbon chain and a water-soluble non-ionic or ionic group. At equilibrium, the concentration of a surfactant solute at the phase interface is greater than its concentration in the bulk of the solution. At a critical surfactant concentration (CMC-critical micelle concentration) the surfactant forms aggregates called micelles. Surfactant solutions exhibit combinations of detergency, foaming, wetting, emulsifying, solubilizing and dispersing properties.

Surfactants are classified depending on the charge of the surface-active moiety. In anionic surfactants, this moiety carries a negative charge. In cationic surfactants, the charge is positive. In nonionic surfactants there is no charge. In amphoteric surfactants solubilization is provided by the presence of positive and negative charges in the molecule.

An old and well-accepted method to determine functionality of surfactants is known as the hydrophile -lipophile balance (HLB). The HLB is an expression of the relative simultaneous attraction of a surfactant for water and for oil. The HLB of a surfactant determines the type of an emulsion that tends to be formed. It is an indicative of the behavior characteristics and not an indication of surfactant efficiency. Within one or two HLB units, the ranges result in the following applications:

| Solubility in water | HLB Value | Application | |
|---|---|---|---|
| Not dispersible | 1 | | |
| | 2 | | |
| | 3 | | |
| | 4 | Water-in-oil emulsifier | |
| Poor dispersion | 5 | | |
| | 6 | | |
| Unstable milky dispersion | 7 | | |
| | 8 | Wetting agent | |
| | 9 | | |
| Stable milky dispersion | 10 | | |
| | 11 | | |
| Translucent-to-clear dispersion | 12 | | |
| | 13 | | |
| | 14 | Detergent | Oil-in-water emulsifier |
| | 15 | | |
| Clear solution | 16 | | |
| | 17 | Solubilizer | |
| | 18 | | |

The appearance of emulsions is governed essentially by the particle size and by the difference in refractive index of the external and internal phases. Transparency may be gained either by having both phases of the same refractive index or by virtue of the internal phase being dispersed in such small particles that refraction does not occur because the particle size of the emulsion is several times smaller than the wavelength of light.

| Particle Size | Appearance |
|---|---|
| Macroglobules | Two phases |
| Greater than 1u | Milky - white emulsion |
| 1 to about 0.1u | Blue - white emulsion |
| 0.1 to about 0.05u | Semitransparent |
| 0.05u and less | Transparent |

The ability to form a small particle (0.05u or less) micelle containing a relatively water insoluble biocide essential oil is a major advantage in improving its efficacy in killing bacteria found in the mouth and other areas. The transparent appearance is of an aesthetic nature for the consumer.

It is also understood in the teaching of this invention that combinations of surfactants can be used to arrive at HLB's that are useful to form the transparent or semi-transparent emulsions. When two or more surfactants are to be blended the HLB of the combinations is easily calculated. If x is the proportion of one surfactant having an HLB of A, and the other surfactant has an HLB of B, the HLB of the combination can be expressed for all practical purposes as xA+ (1−x)B. This is a straight-line relationship. If the value of this 16 or greater, then most likely the combination will be workable.

In a further embodiment of the antimicrobial solution of this invention, selective organic acids are included to enhance the overall efficacy. It is known that certain compositions, e.g., sodium benzoate and sodium salicylate (U.S. Pat. No. 4,657,758) enhance the removal of plaque from the dental rinse formulation.

Additional organic acids helpful to enhance biofilm removal are hydroxy carboxylic, e.g., lactic acid, and mandelic acid as disclosed in U.S. Pat. No. 5,942,480. Salicylic acid is also a hydroxy carboxylic acid.

All of the above organic acids have to varying degrees, antimicrobial activity. They also function as pH buffering agents, if needed.

Where applicable any of the above components when possessing optical activity can be either a racemic mixture or an optically active stereoisomer.

Effective amounts can range from 0.2 to 2.0 weight %.

Another optional ingredient, which can be included in the antimicrobial solutions of this invention, is a compound selected from the various chelating compounds. Chelators are widely used as preservative agents in many OTC formations. At the cellular level, the chelator sequesters divalent cations that are important for cell survival, such as calcium, from the lipid bilayer and from the cell interior. Lack of calcium alters the fluidity of the cell membrane, impairs calcium - dependent metabolic processes, and ultimately results in the death of the cell.

Examples of chelators are ethylenediamine tetra acetic acid (EDTA), ethylene glycol-bis (B-aminoethyl ether)-N,N,N',N'-tetraacetic acid (EGTA), 2,2'-(ethylenediimino) - dibutyric acid (EBAA) and nitrilo triacetic acid (NTA).

Other chelators useful for this invention include phosphino polycarboxylic acid, diethylenetriamine pentaacetic acid, amino tris (methylene phosphonic acid, polyaspartic acid, hydroxyethane diphosphonic acid, and the like. The amount of chelator can vary, but a preferred range for this invention is from about 0.10 to about 1.0 weight %.

Many of the antiseptic mouthwashes contain high levels of ethanol, some as high as 26.9% by volume based on the total volume. Previously, mouthwashes using essential oils would lose some of their potency. However, this invention allows the formulator considerable leeway either to use no alcohol or to use reduced amounts, e.g., 5 to 20% volume. This is a considerable feat as exemplified by U.S. Pat. No. 5,891,422 where the reduction of ethanol was only from about 2–7% by volume.

In addition to ethanol, other alcohols can be used at much lower concentrations not to exceed 5% by volume. Some examples are propanol, isopropanol, benzyl alcohol, phenylethyl alcohol, phenoxyethanol or phenoxypropanol.

EXPERIMENTAL RESULTS

An important criteria of this invention is to use a surfactant or surfactants which will form a transparent or semi-transparent emulsion with micelle formation of the essential oils having a particle size of about 0.05u. It was determined by careful studies, that the HLB of the surfactant (s) should be of about 16 or greater. Since there are literally thousands of surfactants, many of which fulfill these criteria, it would be a very difficult task to examine every one of them on an individual basis. However, the concept of having an HLB of about 16 or greater is important in order to carry out the scope of this invention. Essential oils used were:

| | |
|---|---|
| thymol | 0.064 wt. % |
| eucalyptol | 0.092 wt. % |
| methyl salicylate | 0.060 wt. % |
| menthol | 0.042 wt. % |

It was found experimentally that higher concentrations of the essential oils could be used when using the surfactants described in this invention. In many cases twice as much, or even more.

The following surfactants were found to give the desired results.

| Surfactant (2 wt. %) | | HLB Value |
|---|---|---|
| Phospholipid CDM | (cationic) | >20 |
| Igepal CO-850 | (nonionic) | 16 |
| Atlas G-5000 | (nonionic) | 16.9 |
| Pluronic F-127 | (nonionic) | 22.0 |
| Pluronic P-65 | (nonionic) | 17.0 |
| Tween 20 | (nonionic) | 16.7 |
| DL-2-pyrrolidone-5-carboxylic acid salt of ethyl N-cocoyl-L-arginate | (cationic) | >20 |
| Tagat L | (nonionic) | 17.0 |
| Tagat 5 | (nonionic) | 16.4 |
| Varonic LI-67 | (nonionic) | 18.0 |
| Tego Betaine ZF | (amphoteric) | 20.0 |
| Dodecyl sulfate, sodium salt | (anionic) | ~40 |
| Tetronic 1107 | (nonionic) | 24 |

It was found experimentally that combinations of surfactants resulted in clear transparent emulsions of the essential oils of this invention. This additive relationship is true even if one of the surfactant has an HLB of less than 16. As long as the linear additive relationship is satisfied e.g., XA+(1–x)B where x is the proportion of one surfactant having an HLB of A, and the other surfactant has an HLB of B. If this value is 16 or greater a semi-transparent or transparent emulsion will result.

EXAMPLE

Tween 60 has a HLB of 14.9. When used at 1 to 2 wt. % with the four essential oils used as the recipe for this invention, a milky looking emulsion is produced. However, when Tween 60, at 1 weight % is used in conjunction with Phospholipid CDM at either 0.5 to 1.0 wt. % a transparent emulsion is formed. This combination of two surfactants one having an HLB below 16 and one having an HLB greater than 20 gave a satisfactory transparent emulsion because the combination of the two surfactants yields an HLB greater than 16.

It is an obvious extension that two or more surfactants having HLB's of 16 or greater can be utilized in the teaching of this invention as well.

It may be advantageous to use combinations of surfactants, e.g., Phospholipid or DL-2-pyrrolidone-5-carboxylic acid salt of ethyl N-cocoyl-L-arginate would enhance the antimicrobial activity against certain microorganisms while the addition of dodecylsulfate, sodium salt would enhance the removal of biofilm.

ANTIMICROBIAL ACTIVITY

Using the same recipe of thymol, eucalyptol, methyl salicylate and menthol in conjunction with the surfactants of this invention at 1 to 2 wt. %, the following microorganisms were tested in a standard In Vitro Kill Kinetics Activity test. Time is given minutes.

| Composition | S. mutans ATCC25175 | F. nucleatium ATCC 10953 | C. Albicans ATCC 18804 |
|---|---|---|---|
| Essentials oils | | | |
| 1 wt. % Tego Betaine ZF 1 wt. % dodecyl sulfate, salt Essential oils | <1.0 | <1.0 | <1.0 |
| 1.5 wt. % DL-2-pyrrolidone-5-carboxylic acid salt of ethyl N-cocoyl-L-aryinate Essential oils | <1.0 | <1.0 | <1.0 |
| 1 wt. % Tween 20 0.5 wt. % Phospholipid CDM Essential oils | <1.0 | <1.0 | <1.0 |
| 2 wt. % Pluronic F-127 Essentials oils | <1.0 | <1.0 | <1.0 |
| 1 wt. % Emsorb 2726 1 wt. % Plantaren 2000 Essential oils | <1.0 | <1.0 | <1.0 |
| 2 wt. % Tween 20 Essential oils | <1.0 | <1.0 | <1.0 |
| 2 wt. % Varonic LI-67 Essential oils | <1.0 | <1.0 | <1.0 |
| 1.5 wt. % dodecyl sulfate sodium salt | <1.0 | <1.0 | <1.0 |

Table II illustrates enhanced antimicrobial activity due to utilizing the proper surfactant concentration having a HLB of 16 or larger. This results in the formation of very small particles, about 0.05u or less, of the essential oils. By forming this size of micelle, it gives the oil a maximum surface area with surface tension reducing properties. This allows the essential oils to move easily penetrate the outer membrane of the microorganism yielding a faster kill rate.

Using the same recipe described in the patent application of thymol, eucalyptol, methyl salicylate and menthol with surfactants having HLB of 16 or greater, and different concentrations, it was determined experimentally that a critical range of surfactants produce a superior antimicrobial effect. In all cases 0.12 wt % of the essential oils was used.

TABLE II[1]

| | (tests done at 20, 60 and 90 seconds) | | |
|---|---|---|---|
| Surfactant HLB Concentration | S. Mutans (Gram Positive) | F. Nucleatium (Gram Negative) | C. Albicans (fungus) |
| Igepal CO-850 16 0.5 wt % | <60 | <60 | <90 |
| Igepal CO-850 16 0.5 wt % | <30 | <30 | <30 |
| Dodecyl sulfate sodium salt ~40 0.5 wt % | <60 | <60 | <90 |
| Dodecyl sulfate sodium salt ~40 2.00 wt % | <30 | <30 | <30 |

[1]standard in Vitro Kinetics Activity Tests

Table I illustrates the criticality of having the proper HLB to achieve both the desired appearance (clear), and the optimum essential particle size.

TABLE I

| Chemical Name & Trade Name | HLB | Appearance | Estimated Particle Size |
|---|---|---|---|
| Glycol stearate LIPO EGDS | 2.0 | 2 phase | very large[1] |
| Glyceryl dilaurate Lexemul GDL | 2.4 | not dispersible | very large[1] |
| Ethoxylate Amines Tomah E-14-5 | 5.0 | poor dispersion | >1u |
| PO/EO block polymer Pluronic L62 | 7.0 | poor dispersion | >1u |
| Ethoxylate nonyphenol Tergitol NP-6 | 10.9 | milky dispersion | ~1u[2] |
| Citric ester of monoglycerides Imivitor 370 | 13.0 | translucent | ~1u |
| Alkoxylate alcohol Atlas G-5000 | 16.9 | transparent | ≧0.05u |
| Cocamidopropyl betaine Tego Betain ZF | 20.0 | transparent | ≧0.05u |

[1]particle size of the micelle has no meaning in a two-phase system.
[2]does not meet the criteria of this invention having the desired particle size of about 0.05u or smaller.

What is claimed:

1. A method to prepare an essentially aqueous antimicrobial essential oil solution for topical or oral administration comprising:

a) from about 0.02 to about 2.00 weight percent of antimicrobial essential oils; and b) from about 0.75 to about 2.25 weight percent of a surfactant or combination of surfactants having a hydrophilic-lipophilic balance of about 16 or higher, wherein an essentially clear solution is formed containing the essential oils in the form of micelles having a particle size of about 0.05 microns or less.

2. The method of claim 1 wherein the antimicrobial essential oils consist of the following:

a) thymol from about 0.005 to about 0.600 weight %, b) eucalyptol from about 0.005 to about 0.200 weight %, c) menthol from about 0.005 to about 0.200 weight % d) methyl salicylate from about 0.005 to about 0.300 weight %.

3. The method of claim 1 wherein the surfactants are chemically classified as cationic, anionic, nonionic, amphoteric or mixtures thereof.

4. The method of claim 3 wherein in the total surfactants amount is from about 0.75 to about 2.25 weight percent.

5. The method of claim 1 wherein, optionally from about 2 to about 20 volume percent of an alcohol is added to the antimicrobial essential oil solution.

6. The method of claim 5 wherein the alcohol can be ethanol, propanol, isopropanol, benzyl alcohol, phenoxyethanol or phenoxypropanol or mixtures thereof.

7. The method of claim 1 wherein, optionally from about 0.10 to about 1.0 weight percent of a water soluble chelating agent is added to the antimicrobial essential oil.

8. The method of claim 7 wherein the chelating agent is an aminoacetic acid or an aminophosphorus containing acid compound.

9. The method of claim 1 wherein, optionally from about 0.2 to about 2.0 weight percent of an organic acid is added to the antimicrobial essential oil solution.

10. The method of claim 9 wherein the organic acid can be benzoic, sorbic, salicyclic, lactic, glycolic, mandelic or combinations thereof.

11. The method of claim 10 wherein sorbic, lactic, glycolic, mandelic acids can be a racemic mixture or an optically pure stereoisomer.

12. The method of claim 1 wherein the surfactants are cationic.

13. The method of claim 12 wherein the cationic surfactant is Phospholipid CDM or DL-2-pyrroilidone-5-carboxylic acid salt of ethyl N-cocoyl-L-argenate.

14. The method of claim 13 wherein the surfactants are non-ionic.

15. The method of claim 14 wherein the non-ionic surfactant is a block copolymer or terpolymer of ethylene-propylene oxides.

16. The method of claim 1 wherein the surfactants are anionic.

17. The method of claim 16 wherein the anionic surfactant is dodecyl sulfate or sodium salt.

18. The method of claim 1 wherein the surfactants are amphoteric.

19. The method of claim 18 wherein the amphoteric surfactant is Tego Betaine ZF.

20. The method of claim 1 wherein the antimicrobial essential oils are of an optically pure stereoisomer or a mixture thereof.

21. The method of claim 1 wherein the antimicrobial essential oils are of a geometrically pure stereoisomer or a mixture thereof.

* * * * *